United States Patent [19]

Kato et al.

[11] 4,313,928
[45] Feb. 2, 1982

[54] COMPOSITION FOR LABELING OF RED BLOOD CELLS WITH RADIOACTIVE TECHNETIUM

[75] Inventors: Makoto Kato, Kobe; Masaaki Hazue, Amagasaki, both of Japan

[73] Assignee: Nihon Medi-Physics Co., Ltd., Hyogo, Japan

[21] Appl. No.: 95,789

[22] Filed: Nov. 19, 1979

[30] Foreign Application Priority Data

Nov. 20, 1978 [JP] Japan .................... 53-143956

[51] Int. Cl.$^3$ ............... A61K 43/00; A61K 49/00
[52] U.S. Cl. ............................. 424/1.5; 128/659; 424/9
[58] Field of Search ............ 424/1, 9, 1.5; 128/659

[56] References Cited

U.S. PATENT DOCUMENTS 3,988,429 10/1976 Richards et al. ................ 424/1

FOREIGN PATENT DOCUMENTS 2819319 9/1978 Fed. Rep. of Germany ......... 424/1

OTHER PUBLICATIONS

Kato, J. Nucl. Med., vol. 20, No. 10, Oct. 1979, pp. 1071–1074.
Baker et al., J. Nucl. Med., vol. 16, No. 8, 1975, pp. 720–727.
Kato et al., J. Nucl. Med., vol. 19, No. 4, Apr. 1978, pp. 397–406.
Vyth et al., Chem. Abstracts, vol. 90, No. 9, Feb. 26, 1979, #68536t.
Pavel et al., Chem. Abstracts, vol. 86, No. 19, May 9, 1977, #135624c.
Hamilton et al., Chem. Abstracts, vol. 87, No. 25, Dec. 1977, #196480v.

Primary Examiner—Christine M. Nucker
Attorney, Agent, or Firm—Birch, Stewart, Kolasch & Birch

[57] ABSTRACT

A non-radioactive composition for intracorporeal labeling of red blood cells with radioactive technetium, which comprises as the essential components (a) at least one of pyridoxal and its salts, (b) at least one stannous salt and (c) at least one α-amino acid of which the administeration through a vein in a living body can assure an efficient intracorporeal labeling of red blood cells in the living body with radioactive technetium which is subsequently administered through the vein.

4 Claims, No Drawings

COMPOSITION FOR LABELING OF RED BLOOD CELLS WITH RADIOACTIVE TECHNETIUM

BACKGROUND OF THE INVENTION

The present invention relates to a non-radioactive composition useful for labeling red blood cells with radioactive technetium, and its preparation and use. More particularly, it relates to a non-radioactive composition being useful for the efficient attainment of intracorporeal labeling of red blood cells in living bodies with radioactive technetium, and having a high stability, and no material toxicity, and its preparation and use.

Radioactive substances which are not taken into any organ when administered into blood vessels and which remain in the blood circulation system are useful for obtaining medically valuable information, for instance, for extracorporeal observation of blood pool in the heart and of cerebral and peripheral blood vessels and for determination of the volume of the whole blood circulation system. For development of such radioactive substances, a variety of investigations have been made in the field of nuclear medicine. $^{131}$I-Labeled human serum albumin ($^{131}$I-HSA) is now widely used for such purposes, but this labeled agent is not satisfactory because $^{131}$I has a long half life (i.e. about 8 days) and emits a β-ray which gives a high radiation exposure to patients. In addition, its γ-ray energy spectrum is not suitable for widely employed γ-cameras for low energy.

Since technetium-99m ($^{99m}$Tc) emits only a γ-ray of about 140 KeV (not accompanied with γ-ray) and has a short half life (i.e. about 6 hours), it is quite suitable as a radioactive nuclide for diagnostic agents to be administered to human bodies, and its utilization in the field of nuclear medicine has been rapidly increased in recent years.

Attempts have been made to label the blood circulation system with $^{99m}$Tc in place of $^{131}$I-HSA, and the production of $^{99m}$Tc-HSA and $^{99m}$Tc-red blood cells by the extracorporeal labeling method have been proposed. However, $^{99m}$Tc-HSA is inferior in labeling efficiency and stability in living bodies. $^{99m}$Tc-red blood cells by the extracorporeal labeling method are also not satisfactory because of the complexity of a series of operations necessary for its production: i.e. collection of blood, separation of blood cells, addition of stannous compound, addition of pertechnetate ($^{99m}$Tc), reaction, isolation and purification, and administration. In addition, there is a high possibility of bacterial contamination during the operations. Thus, the use of these labeling agents is not yet widely accepted.

On the other hand, intracorporeal labeling of red blood cells with $^{99m}$Tc has been attempted by administering into a blood vessel an injectable liquid composition containing a stannous compound in the form of phosphate chelate and then administering a pertechnetate ($^{99m}$TcO$_4^-$) so as to lael red blood cells with $^{99m}$Tc specifically. This procedure of labeling has been attracting much interest because of its simplicity and high labeling efficiency, the high stability after labeling, etc. As the stannous phosphate chelate to be used in this procedure, there have been suggested stannous pyrophosphate (Sn-PPi), stannous ethane-1-hydroxy-1,1-diphosphonate (Sn-EHDP), stannous methylenediphosphonate (Sn-MDP), etc. Among them, Sn-PPi is employed most frequently.

SUMMARY OF THE INVENTION

The main object of the present invention is to provide a novel composition for attaining efficient intracorporeal $^{99m}$Tc-labeling of red blood cells with a high stability and no material toxicity. Another object of this invention is to provide a process for industrial preparation of such a composition. A further object of the invention is to provide a method for intracorporeal $^{99m}$Tc-labeling of red blood cells in living bodies with such a composition.

The composition for labeling of the present invention comprises pyridoxal or its salt, a stannous salt and an α-amino acid as the essential components.

As the salts of pyridoxal, there may be used salts with inorganic acids such as monobasic inorganic acids (e.g. hydrochloric acid, nitric acid) and polybasic inorganic acids (e.g. sulfuric acid, phosphoric acid) and with organic acids such as acetic acid and oxalic acid. The stannous salts include the salts of divalent tin ion (Sn$^{++}$), examples of which are stannous halides (e.g. stannous chloride, stannous fluoride), stannous sulfate, stannous nitrate, stannous acetate, stannous citrate, stannous tartrate, etc. The α-amino acid may be a natural or synthetic D-, L- or DL- amino acid having an amino group at the α-position to a carboxyl group. For administration to human bodies, a natural L-amino acid is desirable. In addition to the said essential components, there may be incorporated as a stabilizing agent, a compound having an oxidation-preventing activity such as ascorbic acid. An isotonization agent such as sodium chloride and a preservative such as benzyl alcohol may also be added without any disadvantage. The order of incorporation of the essential and optional components has no influence upon production of the composition of the invention, and those components may be admixed in an optional order. The pH value of the produced composition is not particularly limited, any optional pH value being suitable for the purpose of use of the composition, but it is preferred to adjust the pH value within a range of 8 to 9, for instance, by addition of sodium hydroxide or hydrochloric acid.

The molar ratio of pyridoxal or its salt and the α-amino acid may be varied within the range of 0.3 to 3.0. A particularly desirable molar ratio is 1.0. The stannous salt may be used in a sufficient amount to reduce the whole pertechnetate administered into a blood vessel. When the stability of the composition of the invention and the toxicity of the stannous salt are taken into consideration, the stannous salt may be used in an amount of 0.001 to 0.01 mol per 1 mol of pyridoxal or its salt. The concentration of pyridoxal or its salt may not be less than 0.5 mmol/liter insofar as it is sufficiently dissolved to give a clear solution (e.g. not more than 500 mmol/liter). In considering the amount of the stannous salt to be added and the stability of the composition of the invention, a concentration of 80 to 100 mmol/liter is preferable. Although the composition of the invention is usually administered into blood vessels of living bodies and therefore should be ultimately prepared in the form of aqueous solution, it may be formulated in a powdery form at the intermediary stage for the convenience of storage. For instance, the composition of the invention once prepared in an aqueous solution may be subjected to lyophilization, and the lyophilized product may be diluted with water to make an aqueous solution upon use. Alternatively, for instance, an aqueous solution comprising pyridoxal or its salt and a stannous salt or a lyophilized product therefrom and an aqueous solution comprising an α-amino acid or a lyophilized product therefrom may be separately produced and stored as a kit. Upon use, these are combined together, if necessary, with an additional amount of an aqueous medium to make the composition of the invention in the form of an aqueous solution.

For intracorporeal labeling of red blood cells in living bodies with radioactive technetium, the composition of the invention in an aqueous solution form is usually first administered to a blood vessel such as a vein and then an aqueous solution comprising $^{99m}Tc$ in the form of pertechnetate is administered to the blood vessel. The amount of the composition of the invention to be administered may be such that the stannous salt therein can sufficiently reduce $^{99m}Tc$ in the form of pertechnetate to be subsequently administered. When, for instance, the administration is carried out intravenously, the composition of the invention may be employed in such an amount as containing 10 to 20 μg of stannous ion per kg of bodyweight, which corresponds to a 2.0 to 4.0 ml injection of 2.95 mM/liter stannous ion solution to a 70 kg man. In such case, the concentration of $^{99m}Tc$ in the aqueous solution is normally from about 0.1 to 50 mCi in about 0.5 to 5.0 ml at the time of administration. Needless to say, the doses of the composition of the invention and of the $^{99m}Tc$ aqueous solution may be varied with the concentrations of the active ingredients, the bodyweights of the patients, etc. Although no special limitation is present in the time difference between the administrations of the composition of the invention and of the $^{99m}Tc$ aqueous solution, a period of about 10 to 60 minutes, preferably about 15 to 30 minutes, may be put between them.

The composition of the invention is quite suitable for intracorporeal $^{99m}Tc$-labeling of red blood cells because of the following advantageous characteristics:

(1) The composition is stable for a long period of time after the production;

(2) Labeling of red blood cells with $^{99m}Tc$ can be attained in a high yield by a simple operation comprising administration of the composition into a blood vessel and subsequent administration of an aqueous solution of $^{99m}Tc$ in the form of pertechnetate into the blood vessel;

(3) The obtained $^{99m}Tc$-labeled red blood cells are sufficiently stable in living bodies; and (4) The toxicity is extremely low.

The present invention will be explained in further detail by way of the following examples.

EXAMPLE 1

Preparation of a composition for labeling containing L-isoleucine as the α-amino acid and ascorbic acid as the stabilizing agent (this composition being hereinafter referred to as "Sn-P.Ile.A."):

Nitrogen gas, sterilized by passing through a filter of 0.22 μm in pore size, was introduced into pyrogen-free sterile water to eliminate dissolved oxygen therefrom. Into the thus treated water (100 ml), pyridoxal hydrochloride (3665 mg, 18 mmol), anhydrous stannous chloride (37.9 mg, 0.2 mmol) and L-(+)-ascorbic acid as the stabilizer (70 mg, 0.4 mmol) were dissolved under sterile conditions in a nitrogen atmosphere to make a solution (hereinafter referred to as "solution A"). Separately, L-isoleucine (2361 mg, 18 mmol) and sodium hydroxide (1440 mg, 36 mmol) were dissolved into the said sterile, pyrogen-free and oxygen-free water (100 ml) under sterile conditions in a nitrogen atmosphere to make a solution (hereinafter referred to as "solution B"). The solutions A and B were mixed together in a nitrogen atmosphere to obtain the objective composition for labeling, Sn-P.Ile.A., which was filled in portions (each 2.0 ml) into vials having a rubber cap through a filter of 0.22 μm in pore size in a nitrogen atmosphere. The thus obtained Sn-P.Ile.A. is a clear yellow solution having a pH value of 8 to 9.

EXAMPLE 2

Preparation of compositions for labeling containing α-amino acids other than L-isoleucine:

In the same manner as in Example 1 but using L-leucine, L-valine, L-phenylalanine, L-alanine, L-glycine, and monosodium L-glutamate in place of L-isoleucine in the same molar amount (18 mmol), compositions for labeling (i.e. Sn-P.Leu.A., Sn-P.Val.A., Sn-P.Phe.A., Sn-P.Ala.A., Sn-P.Gly.A. and Sn-P.Glu.A.) were prepared. These compositions were each a clear yellow solution having a pH value of 8 to 9.

EXAMPLE 3

Lyophilization of compositions for labeling obtained in Examples 1 and 2:

The Sn-P.Ile.A. solution obtained in Example 1 was charged in portions (each 2.0 ml) into vials for lyophilization and subjected to lyophilization by the aid of a lyophilizer. After the lyophilization, the pressure was elevated to atmospheric pressure by the introduction of nitrogen, and the vials were sealed with a rubber cap in a nitrogen atmosphere.

The compositions for labeling obtained in Example 2 were also treated in the same manner as above for lyophilization.

EXAMPLE 4

Production of a kit for preparation of a composition for labeling (Sn-P.Ile.A.) on use:

The solution A obtained in Example 1 was charged in portions (each 1.0 ml) into vials for lyophilization through a filter of 0.22 μm in pore size in a nitrogen atmosphere and subjected to lyophilization by the aid of a lyophilizer. After the lyophilization, the pressure was elevated to atmospheric pressure by the introduction of nitrogen, and the vials were sealed with a rubber cap in a nitrogen atmosphere to obtain a preparation (hereinafter referred to as "Sn-P.A."). Separately, the solution B obtained in Example 1 was diluted two fold with sterile, pyrogen-free and oxygen-free water (100 ml) with sufficient stirring. The diluent was filled in portions (each 2.5 ml) into ampoules through a filter of 0.22 μm in pore size in a nitrogen atmosphere and melt-sealed in a nitrogen atmosphere to obtain another preparation (hereinafter referred to as "Ile."). On use, Ile. (2.0 ml) is added to Sn-P.A. to obtain Sn-P.Ile.A.

EXAMPLE 5

Production of kits for preparation of compositions for labeling on use:

In the production of the solution B described in Example 1, L-leucine, L-valine, L-phenylalanine, L-alanine, L-glycine and L-monosodium glutamate were used in place of L-isoleucine in the same molar amount to obtain preparations Leu., Val., Phe., Ala., Gly. and Glu. On use, each of these preparations (2.0 ml) is added to Sn-P.A. obtained in Example 4 to obtain Sn- P.Leu.A., Sn-P.Val.A., Sn-P.Phe.A., Sn-P.Ala.A., Sn-P.Gly.A. and Sn-P.Glu.A.

EXAMPLE 6

Intracorporeal $^{99m}$Tc-labeling of red blood cells with compositions for labeling:

The composition for labeling of the invention was injected into the tail vein of female rats of Sprague-Dawley strain (body weight, 145–175 g). The dose of the composition for labeling was adjusted so that the amount of Sn(II) per 1 kg of body weight was 20 μg (as mentioned below). After a designated time (30 minutes), a normal saline solution (0.2 ml) containing $^{99m}$Tc in the form of sodium pertechnetate (about 0.5 mCi) was injected into the opposite tail vein. One hour after the administration of $^{99m}$Tc, the rats were subjected to abdominal incision, and blood (5–7 ml) was collected from aorta with a heparinized syringe. A part of the collected blood (1.0 ml) was put into an ampoule for radioactivity determination with a pipet and counted on a gamma counter. By comparing the determined value thus obtained with that of a separately prepared standard sample, the percentage of $^{99m}$Tc present in 1 ml of blood (after corrected with decay) to the whole injected dose was calculated. This value was indicated as % ID/ml Blood (ID=injected dose). For comparison of the data obtained in animals having different body weights, this value was then normalized to an average body weight of 160 g according to the following equation:

$$\% \ ID/\text{ml Blood (norm)} = [\% \ ID/\text{ml Blood}] \times \frac{W}{160}$$

W: body weight of rat (g)

The remaining blood (3 to 5 ml) was centrifuged (800 g, 20 min) to be separated into plasma and blood cells. After centrifuging, the hematocrit value (volume percent of blood cells in blood, % Hct) was obtained. A part of the separated plasma (1.0 ml) was placed into an ampoule for radioactivity determination with a pipet. The plasma (1.0 ml) and the above mentioned blood (1.0 ml) were counted in the same geometrical position (the same count efficiency position) in the gamma counter, and from the determined values, the background values were subtracted to obtain net count values per 1 min., C(plasma) and C(blood). From these values, the percentages of radioactivity distributed in the red blood cells and in the plasma (%/RBC and %/Plasma, respectively) were calculated according to the following equations:

$$\%/\text{Plasma} = \frac{C(\text{Plasma}) \times \left(1 - \frac{\%Hct}{100}\right)}{C(\text{Blood})} \times 100$$

$$\%/RBC = 100 - (\%/\text{Plasma})$$

Then, the percentage of radioactivity present in 1 ml of red blood cells to the whole dose of radioactivity [%/ml RBC (norm)] was calculated according to the following equation:

$$\%ID/\text{ml } RBC \text{ (norm)} = [\%/\text{ml Blood (norm)}] \times \frac{(\%/RBC)}{(\%/Hct)}$$

Finally, the percentage of radioactivity present in the whole red blood cells to the whole dose of radioactivity (%ID in whole RBC) was calculated according to the following equation, on the assumption that the whole amount of blood (ml) was 6.5% of the body weight (g):

%ID in whole RBC $$= [\%ID/\text{ml Blood}] \times W \times \frac{6.5}{100} \times \frac{(\%/RBC)}{100}$$

$$= [\%ID/\text{ml Blood (norm)}] \times 160 \times \frac{6.5}{100} \times \frac{(\%/RBC)}{100}$$

Using the experimental procedure described above, the following evaluations were performed on the compositions of the invention:

(1) The results of intracorporeal labeling of red blood cells with seven kinds of the compositions for labeling of the invention are shown in Table 1.

TABLE 1

Intracorporeal $^{99m}$Tc-labeling of red blood cells with compositions for labeling:-

| Composition for labeling | % ID/ml Blood (norm) | %/RBC | %/Plasma | % ID/ml RBC (norm) | % ID in whole RBC |
|---|---|---|---|---|---|
| Sn-P.Ile.A. | 9.58 | 98.95 | 1.05 | 20.77 | 98.52 |
| Sn-P.Val.A. | 9.05 | 99.04 | 0.96 | 19.62 | 93.05 |
| Sn-P.Leu.A. | 8.79 | 98.98 | 1.02 | 19.09 | 90.51 |
| Sn-P.Phe.A. | 8.75 | 98.90 | 1.10 | 18.98 | 90.01 |
| Sn-P.Ala.A. | 9.51 | 98.99 | 1.10 | 20.64 | 97.94 |
| Sn-P.Gly.A. | 9.51 | 98.71 | 1.29 | 20.60 | 97.71 |
| Sn-P.Glu.A. | 9.34 | 98.75 | 1.25 | 20.23 | 96.00 |
| Sn-PPi* | 8.38 | 98.70 | 1.30 | 18.17 | 86.18 |

Note: Each numeral indicates an average value for five rats.

For comparison, the results obtained in the already known Sn-PPi (*) used under the same conditions are also shown in Table 1. In this experiment, each of the compositions for labeling was administered in an amount of 20 μg as Sn(II) ion per 1 kg of body weight of rat, then $^{99m}$TcO$_4^-$ was administered after 30 minutes and the blood was collected 1 hour thereafter. With the amount of Sn(II) of 20 μg/kg, as mentioned below, the efficiency of labeling of red blood cells reached the maximum in each of the compositions for labeling. As understood from Table 1, all of the compositions for labeling of the invention showed a labeling efficiency of 90% or more in the %ID in whole RBC.

From these results, it will be apparent to those skilled in the art that a series of the compositions for labeling of the invention exhibit an extremely excellent property in intracorporeal labeling of red blood cells with $^{99m}$Tc.

(2) The relationship between the dose of Sn-P.Ile.A. as a typical representative of the composition for labeling of the invention and the efficiency of intracorporeal labeling of red blood cells is shown in Table 2.

TABLE 2

Intracorporeal $^{99m}$Tc-labeling red blood cells with Sn-P.Ile.A.:-

| Amount of Sn (II) (μg/kg body weight) | % ID/ml Blood (norm) | %/RBC | %/Plasma | % ID/ml RBC (norm) | % ID in whole RBC |
|---|---|---|---|---|---|
| 1 | 1.12 | 40.16 | 59.04 | 0.98 | 4.64 |
| 5 | 6.26 | 98.38 | 1.62 | 13.50 | 64.03 |
| 10 | 9.52 | 99.10 | 0.90 | 20.68 | 98.08 |
| 20 | 9.58 | 98.95 | 1.05 | 20.77 | 98.52 |
| 40 | 8.56 | 98.61 | 1.39 | 18.49 | 87.71 |

Note: Each numeral indicates an average value for five rats

As apparent from this Table, administration of 10 to 20 μg/kg of Sn(II) in the form of Sn-P.Ile.A. attains a high yield of red blood cell labeling. Similar results were also obtained on the compositions for labeling other than Sn-P.Ile.A. shown in Example 2.

It was shown by these experiments that intracorporeal labeling of red blood cells with $^{99m}$Tc could be realized with extreme simplicity by the use of the composition for labeling of the invention.

EXAMPLE 7

Stability of compositions for labeling:
(1) Stability in a solution form:

The Sn-P.Ile.A. produced as in Example 1 was stored at 4° to 8° C. for 50 to 100 days. By the use of the resulting preparation, the intracorporeal labeling of red blood cells with $^{99m}$Tc was effected as in Example 6. The results are shown in Table 3. As apparent from this Table, Sn-P.Ile.A. in a solution form is extremely stable, not showing any sign of degradation during a period immediately after its production to the 100th day.

It was also confirmed that many kinds of compositions for labeling of the invention including the other six compositions shown in Example 2 showed a similar stability in a solution form.

TABLE 3

Stability of Sn-P.Ile.A. in a solution form (stored at 4 to 8° C.):-

|  | After production | |
| --- | --- | --- |
|  | 50 days | 100 days |
| % ID/ml Blood (norm) | 9.57 | 9.52 |
| %/RBC | 98.26 | 98.32 |
| %/Plasma | 1.74 | 1.68 |
| % ID/ml RBC (norm) | 20.21 | 20.11 |
| % ID in whole RBC | 98.22 | 98.16 |

Note: Average values for five rats

Experimental procedure: administration of Sn-P.Ile.A. in an amount of 20 μg as Sn(II) per 1 kg of the body weight of a rat, further administration of $^{99m}$TcO$_4^-$ after 30 minutes and collection of blood 1 hour thereafter.

(2) Stability in a lyophilized state

The lyophilized product of Sn-P.Ile.A. produced as in Example 3 was stored at 4° to 8° C. for 100 or 200 days. Using the resultant product, the intracorporeal labeling of red blood cells with $^{99m}$Tc was effected as in Example 6. The results are shown in Table 4.

TABLE 4

Stability of Sn-PIle.A. in a lyophilized state (stored at 4 to 8° C.):-

|  | After production | |
| --- | --- | --- |
|  | 100 days | 200 days |
| % ID/ml Blood (norm) | 9.63 | 9.52 |
| %/RBC | 98.42 | 98.31 |
| %/Plasma | 1.58 | 1.69 |
| % ID/ml RBC (norm) | 20.24 | 20.21 |
| % ID in whole RBC | 98.31 | 98.35 |

Note: Average values for five rats

Experimental procedure: administration of Sn-P.Ile.A. in an amount of 20 μg as Sn(II) per 1 kg of the body weight of a rat, further administration of $^{99m}$TcO$_4^-$ after 30 minutes and collection of blood 1 hour thereafter.

The lyophilized product was subjected to the experiment in the form of a solution which was prepared by adding distilled water for injection (2.0 ml) immediately before the use. As apparent from Table 4, the Sn-P.Ile.A. in a lyophilized state is extremely stable, not showing any sign of degradation during the period immediately after its preparation to the 200th day.

It was also confirmed that many kinds of compositions for labeling of the invention including the other six compositions shown in Example 3 showed a similar stability in a lyophilized state.

(3) Stability of a kit for preparation of a composition for labeling:

A kit for preparation of a composition for labeling comprising Sn-P.A. and Ile. which was produced as in Example 4 was stored at 4° to 8° C. for 100 or 200 days. Immediately before the use, Ile (2.0 ml) was added to Sn-P.A. to obtain Sn-P.Ile.A., by the use of which the intracorporeal labeling of red blood cells with $^{99m}$Tc was effected as in Example 6. The results are shown in Table 5. As apparent from this Table, the kit for preparation of a composition for labeling comprising Sn-P.A. and Ile. is extremely stable, not showing any sign of degradation during the period from its production time to the 200th day.

TABLE 5

Stability of a kit for preparation of a composition for labeling comprising Sn-P.A. and Ile. (stored at 4 to 8° C.):-

|  | After production | |
| --- | --- | --- |
|  | 100 days | 200 days |
| % ID/ml Blood (norm) | 9.55 | 9.49 |
| %/RBC | 98.43 | 98.66 |
| %/Plasma | 1.57 | 1.34 |
| % ID/ml RBC (norm) | 20.41 | 20.52 |
| % ID in whole RBC | 99.22 | 99.24 |

Note: Average values for five rats.

Experimental procedure: administration of Sn-P.Ile.A. in an amount of 20 μg as Sn(II) per 1 kg of the body weight of a rat, further administration of $^{99m}$TcO$_4^-$ after 30 minutes and collection of blood 1 hour thereafter.

It was also confirmed that many kinds of kits shown in Example 5 showed the same stability

EXAMPLE 8

Toxicity of compositions for labeling of the invention:

In the same manner as in Example 1 or 2 but using the materials other than water in amounts of 5 times, there were produced seven kinds of compositions for labeling having 5 fold concentrations in comparison with the concentrations of the compositions for labeling obtained in Example 1 or 2. Each of the resulting solutions was intravenously administered to groups consisting of 10 Sprague Dawley strain male rats, of 10 S-D strain female rats, of 10 ICR strain male mice and of 10 ICR strain female mice at a dose of 0.5 ml per 100 g of body weight (corresponding to an amount of 1000 fold the designed dose to human beings) as well as to groups consisting of 100 Hartley strain male guinea pigs, of 10 Hartley strain female guinea pigs, of 10 male rabbits and of 10 female rabbits at a dose of 0.25 ml per 100 g of body weight (corresponding to an amount of about 500 folds the designed dose to human beings (per unit body weight)). As a control, the same volume of a normal saline solution was intravenously administered to separate groups of the same kinds of animals as above. These animals were fed and observed for 10 days, and changes in the body weight were recorded every day.

As the result of this toxicity test, no significant difference in the appearance of the animals and the change of the body weight was recognized between the groups treated with the composition for labeling and the control groups. After 10 days of feeding and observation, all the animals were subjected to dissection, and observation of various organs was effected to examine histological abnormalities, whereby no abnormality was seen in any of the animals.

As shown from these results of the toxicity test, the composition for labeling of the invention produces no abnormality, even when administered to four kinds of animals (both male and female) in an amount of 500 to 1000 folds the designed dose to human beings per unit body weight. Thus, its toxicity is proven to be extremely low.

It should be understood by those skilled in the art that the above mentioned Examples are intended only to illustrate and explain the invention in detail and not to limit the scope of the invention.

What is claimed is:

1. A method for the intracorporeal labeling of red blood cells in a living body with radioactive technetium, which comprises:
    administering into a blood vessel of the living body an aqueous solution of a non-radioactive composition comprising as the essential components (a) at least one of pyridoxal and its salts, (b) at least one stannous salt and (c) at least one α-amino acid and
    subsequently administering into a blood vessel of the living body an aqueous solution of radioactive technetium, whereby the red blood cells are specifically labeled with radioactive technetium.
2. The method according to claim 1, wherein the blood vessel is a vein.
3. The method according to claim 1, wherein the amount of said non-radioactive composition is present in an amount to sufficiently reduce the $^{99m}Tc$ in the form of pertechnetate which is subsequently administered.
4. The method according to claim 1, wherein said radioactive technetium is administered 10 to 60 minutes after said non-radioactive composition.

* * * * *